United States Patent [19]

Zacca et al.

[11] Patent Number: 5,217,474
[45] Date of Patent: Jun. 8, 1993

[54] EXPANDABLE TIP ATHERECTOMY METHOD AND APPARATUS

[76] Inventors: Nadim M. Zacca, 6550 Fannin St., Suite 2229, Houston, Tex. 77030; Martin R. Jasso, 5 Nottingham Dr., Queensbury, N.Y. 12804

[21] Appl. No.: 731,109
[22] Filed: Jul. 15, 1991
[51] Int. Cl.⁵ .............................................. A61B 17/32
[52] U.S. Cl. .................................. 606/159; 606/170; 606/180
[58] Field of Search ............... 606/159, 170, 180, 191, 606/194, 198, 200; 604/22, 104–109; 15/104.01 R, 104.16, 104.33

[56] References Cited

U.S. PATENT DOCUMENTS

| | | |
|---|---|---|
| 2,541,691 | 2/1951 | Eicher . |
| 2,730,101 | 1/1956 | Hoffman . |
| 2,816,552 | 1/1957 | Hoffman . |
| 3,283,353 | 11/1966 | Kirk ................................. 15/104.33 |
| 3,749,085 | 7/1973 | Willson et al. . |
| 4,030,503 | 6/1977 | Clark, III .............................. 606/159 |
| 4,445,509 | 5/1984 | Auth . |
| 4,646,736 | 3/1987 | Auth . |
| 4,653,496 | 3/1987 | Bundy et al. ........................ 606/159 |
| 4,655,217 | 4/1987 | Reed . |
| 4,706,671 | 11/1987 | Weinrib ................................ 606/159 |
| 4,762,130 | 8/1988 | Fogarty et al. . |
| 4,765,332 | 8/1988 | Fischell et al. . |
| 4,794,928 | 1/1989 | Kletschka . |
| 4,834,093 | 5/1989 | Littleford et al. . |
| 4,842,579 | 6/1989 | Shiber . |
| 4,885,003 | 12/1989 | Hillstead . |
| 4,895,560 | 1/1990 | Papantonakos . |
| 4,909,781 | 3/1990 | Husted ................................. 606/159 |
| 4,966,604 | 10/1990 | Reiss . |
| 4,979,951 | 12/1990 | Simpson . |
| 4,986,807 | 1/1991 | Farr . |
| 4,990,134 | 2/1991 | Auth . |
| 4,994,067 | 2/1991 | Summers . |
| 5,007,896 | 4/1991 | Shiber . |
| 5,009,659 | 4/1991 | Hamlin et al. . |
| 5,019,088 | 5/1991 | Farr et al. . |
| 5,019,089 | 5/1991 | Farr . |
| 5,024,651 | 6/1991 | Shiber . |
| 5,026,384 | 6/1991 | Farr et al. . |
| 5,030,201 | 7/1991 | Palestrant . |
| 5,041,082 | 8/1991 | Shiber . |
| 5,042,984 | 8/1991 | Kensey et al. . |
| 5,047,040 | 9/1991 | Simpson et al. . |
| 5,049,154 | 9/1991 | Quadri . |
| 5,053,044 | 10/1991 | Mueller et al. . |
| 5,059,203 | 10/1991 | Husted . |
| 5,071,424 | 12/1991 | Reger . |
| 5,074,841 | 12/1991 | Ademovic et al. . |
| 5,074,871 | 12/1991 | Groshong . |
| 5,078,722 | 1/1992 | Stevens . |
| 5,078,723 | 1/1992 | Dance et al. . |

FOREIGN PATENT DOCUMENTS 0268228 5/1988 European Pat. Off. .

*Primary Examiner*—C. Fred Rosenbaum
*Assistant Examiner*—William Lewis
*Attorney, Agent, or Firm*—William E. Shull; Ned L. Conley; David A. Rose

[57] ABSTRACT

A device for removing obstructions from vessels or small openings in the body, comprising a rotatable ablator tip which is guided to the obstruction in a reduced diameter configuration, expanded and rotated to remove the obstruction, and contracted to remove the device from the body. The variably expandable abrasive tip coil in one embodiment of the invention is actuated by a piston means disposed within the coil. A pair of collars is attached to the ends of the coil, and the piston effects relative longitudinal axial movement of the collars and, hence, the respective ends of the coil tip. When the ends of the coil tip are so moved with respect to one another, expansion and contraction of the diameter of the coil tip results. In another embodiment of the invention, the expansion tip coil is actuated by an expandable and contractible bellows means disposed within the coil, instead of the piston means. In another embodiment of the invention, the expansion and contraction of the coil tip are effected by longitudinal axial movement of an internal coil attached to one end of the coil tip, within an outer coil attached to the other end of the coil tip. In another embodiment of the invention, expansion and contraction of the coil tip are effected by an inflatable balloon disposed within the coil tip. The balloon expansion means enlarges preferably at the central portion of the coil to make a bulge.

40 Claims, 7 Drawing Sheets

EXPANDABLE TIP ATHERECTOMY METHOD AND APPARATUS

BACKGROUND OF THE INVENTION

1. Field of the Invention

The present invention relates in general to devices for removing obstructions from vessels or small openings in the body, and more particularly to a rotatable ablator tip which is guided to the obstruction in a reduced diameter configuration, expanded and rotated to remove the obstruction, and contracted to remove the device from the body.

2. Background Art

There has been great interest of late among those in the medical community in non-surgical means to remove obstructions from occluded vessels, particularly coronary arteries. Traditionally, patients have had to undergo relatively complex, invasive, and risky coronary bypass surgery in order to obviate or reduce the obvious health hazards presented by occluded coronary arteries. Coronary bypass surgery typically involves utilizing vascular tissue from another part of the patient's body, such as his leg, and constructing a shunt around the obstructed vessel. The obstruction can be formed of a relatively hard material, such as a plaque deposit, or a softer material such as a fibrinogen polymerized to form a thrombus.

An alternative to the traditional coronary bypass surgery which has become popular in recent years is a technique known as balloon angioplasty. In this technique, a deflated balloon is introduced by means of a catheter to the obstructed area. The balloon is then inflated to open the lumen of the vessel. The inflated balloon tends to crush or compact the obstructing material against the vessel walls as well as crack the obstructing material and dilate the vessel so as to increase the lumen or passageway therethrough, but does not remove the obstructing material from the vessel. Since the cracked and fractured obstructing material is not removed, there is a significant possibility that the vessel will become reoccluded at the treated area within a relatively short period of time, thus requiring additional treatment(s). The balloon angioplasty procedure has several additional drawbacks which tend to further reduce its desirability and/or effectiveness. In the case of a severely occluded vessel, it may be difficult to position the deflated balloon so that it spans the occlusion without causing undue trauma to the surrounding vasculature. This is because the leading portion of the balloon must first be forced through the occlusion into position for treatment. The balloon angioplasty procedure is not satisfactory for treating calcified and hard occlusions, since it may not be able to crack and dilate the obstructing material. The balloon angioplasty procedure also is not satisfactory for treating eccentric occlusions, i.e., occlusions which occur primarily on one side of the vessel, because the balloon tends to simply stretch the healthy vascular tissue and not to compress the occluding material. After the balloon is deflated, the healthy vascular tissue returns to its normal shape and the occlusion remains essentially untouched. Moreover, the balloon angioplasty technique is less suitable for treating lengthy occlusions or those occurring at curves and bends in the vessels, due to the difficulty of appropriately placing and properly inflating the balloons without the high risk of dissections. In addition, during the balloon angioplasty technique, there is a period of time during which the vessel is essentially totally obstructed by the balloon. This could lead to further damage to tissues already damaged, or even to damage to previously healthy tissues. Moreover, when the balloon inflates, it may cause uncontrolled deep injury to the vessel, including the formation of intraluminal flaps, which may in turn result in abrupt closure or predispose to a high rate of restenosis.

Atherectomy is another technique developed of late for opening the lumen of an occluded vessel, and, like the balloon angioplasty technique, provides an alternative to the traditional coronary bypass surgery. Atherectomy involves physically breaking up the material which blocks or partially blocks the vessel. Several types of atherectomy devices have been developed. U.S. Pat. Nos. 4,990,134 and 4,445,509 to Auth disclose a rotatable burr with a fluted or abrasive surface that is introduced into the obstructed vessel. At the obstruction the burr is rotated at a high rate of speed to abrade or cut away at the obstruction. The burr is a solid tip that is introduced into the vessel with a catheter and remotely driven to rotate at the desired speed. The burr is introduced into the patient's body typically at the femoral artery and guided to the obstructed vessel.

The rotatable burr atherectomy devices of the prior art when properly used have several advantages over the balloon angioplasty technique. Unlike the balloon angioplasty technique, treating an occluded vessel with a rotatable burr essentially completely removes the obstructing material, leaving the vessel wall relatively smooth and eliminating the bits or flaps of tissue at the treatment site which often result from balloon angioplasty. Moreover, unlike the balloon angioplasty device, a rotatable burr can effectively remove eccentric occlusions, because the rotating burr tends to "slide off" the healthy vascular tissue on one side of the vessel and to selectively abrade the occluding material on the other side of the vessel. Furthermore, a rotatable burr, which abrades as it progresses, can effectively treat a relatively long occlusion, and tight and/or calcified occlusions.

One major drawback with traditional rotatable burr atherectomy devices is that they have a fixed working diameter. That is, the cutting size is fixed and cannot be varied to accommodate a range of vessel openings. When it is necessary to clear a relatively large vessel which has become severely occluded, typically a physician will be reluctant to use a burr of sufficient diameter to clear the vessel all at once. This necessitates the use of two or more successively larger diameter burrs. Moreover, many times the prior art atherectomy procedure must be assisted by a balloon procedure in order to achieve an adequate result. The above tends to lengthen and complicate the procedure and make it costly. In order to get a large diameter burr to the site of the obstruction, it must first be introduced into the patient's body through an introducer sheath, typically in the patient's leg, and guided through the patient's vascular system to the obstructed vessel. Large burrs require appropriately large introducer sheaths, which tend to cause increased vascular tissue trauma at the site of introduction. Large burrs also tend to cause increased vascular tissue trauma as they are guided through the patient's vascular system to the obstruction site. Large burrs might also interfere with or disturb other occlusions along the way to the target occlusion, such other occlusions being otherwise too small to indicate treatment. For example, it has been found that it is better not to treat or disturb occlusions of less than about 50%-60%, since treatment of such lesions entails greater risks to the patient's health than leaving them untreated or undisturbed. A large diameter burr could tend to disturb such small lesions in passage, even to the extent that they become health-threatening. In addition, because prior art burrs have had an abrading surface on only their forward or distal surfaces, physicians have encountered difficulty in satisfactorily treating occlusions at curved vessel locations. Accordingly, physicians faced with the prospects of having to introduce, guide, and then manipulate in the obstructed area a relatively large burr might choose to avoid the rotatable burr technique altogether and fall back to a less desirable alternative, such as balloon angioplasty or even bypass surgery.

Thus, there is a clear need in the medical community for an atherectomy device which possesses all the advantages of the traditional rotatable burr device over the balloon angioplasty technique, but yet can be introduced into the patient's body with a relatively small introducer sheath, thus minimizing tissue trauma at the introduction site; can be guided to the obstruction site with minimal vascular tissue trauma and using smaller guiding catheters; can pass through non-targeted (smaller) occlusions with minimal contact; and can be used to treat openings of varying size during the same procedure. It will be appreciated that such a device would eliminate the need for multiple procedures with varying sized burrs, and would eliminate the reluctance of physicians to use the rotatable burr technique in the first place due to the disadvantages they see with the larger, fixed diameter burrs. There is also a need for such a device having an abrading surface on its proximal face as well as on its distal face, to facilitate treating occlusions at curved vessel sites.

Other atherectomy devices with rotatable expandable blades have been disclosed in U.S. Pat. No. 4,966,604 to Reiss and U.S. Pat. No. 4,895,560 to Papantonakos. Although the blades expand to accommodate variable vessel size, sensor devices or other means must be used during the expansion of the instrument and cutting because the blades can injure or puncture the vessel to be repaired in addition to cutting away the obstruction.

SUMMARY OF THE INVENTION

The present invention comprises apparatus and methods for removing obstructions from vessels or small openings in the body. The apparatus is guided into the vessel having the obstruction. The tip of the apparatus comprises a short length of ovaloid shaped coil that can be elongated, thereby decreasing its circumference as compared to its circumference in the normal wound configuration. Lengthening and rotating the coil reduce its circumference and facilitate its introduction to an obstructed area. The coil is then allowed to return to a normal wound configuration thereby increasing the overall circumference of the coil. At least part of the outer surface of the coil is abrasive. The coil can be enlarged to a preselected circumference between the normal wound configuration and the elongated smaller circumference. The coil is rotated at the point of the obstruction to break up the obstruction and clear the vessel. The above ovaloid shaped coil resembles a spiral lemon peel.

Preferably the coil is tightly wound and multifilar, preformed in an ovoid shape. The coil typically surrounds a means for facilitating introduction into the vessel where the obstruction is located, such as a catheter with a lumen for guide wire insertion. The coil is held at one end by a tapered tip at the end of the catheter. The coil is connected to a means for rotation.

The coil diameter can be selectively decreased and increased as desired to reach and treat, respectively, the obstruction in the vessel. The coil's circumference can be increased or decreased over a range by a remotely actuated means that will elongate or retract the coil as desired. This permits the use of introducers and guiding catheters of smaller diameters than is common in the present practice of device introduction, resulting in less trauma to the patient's vessels at the site of introduction and en route to the obstruction, and also simplifying the procedure.

The present invention comprises a variably expandable abrasive tip coil which may be rotated at the point of obstruction. In one embodiment of the invention, the expansion tip coil is actuated by a piston means disposed within the coil. A pair of collars is attached to the ends of the coil, and the piston effects relative longitudinal axial movement of the collars and, hence, the respective ends of the coil tip. When the ends of the coil tip are so moved with respect to one another, expansion and contraction of the diameter of the coil tip results. In another embodiment of the invention, the expansion tip coil is actuated by an expandable and contractible bellows means disposed within the coil, instead of the piston means. In another embodiment of the invention, the expansion and contraction of the coil tip are effected by longitudinal axial movement of an internal coil attached to one end of the coil tip, within an outer coil attached to the other end of the coil tip. In another embodiment of the invention, expansion and contraction of the coil tip are effected by an inflatable balloon disposed within the coil tip. The balloon expansion means enlarges preferably at the central portion of the coil to make a bulge.

The ability of the tip to adjust to a desired diameter, within the maximum and minimum range, permits the progressive, from smaller to larger, enlargement of a passage through a stenotic obstruction. The variable tip diameter permits the use of a single device of the present invention to more fully clear a stenosis without the need to use two or more of the existing fixed diameter atherectomy devices. The present treatment of stenosis, with fixed diameter atherectomy devices, in addition to requiring the use of two or more cutting devices almost always requires the use of an angioplasty balloon catheter as a final treatment. A single device of the present invention will fully treat a stenosis, thus shortening the procedure, reducing trauma, and reducing procedure cost.

After an obstruction is cleared, it is possible to decrease the circumference of the coil by elongation and easily withdraw the coil and associated catheter from the vessel.

The coil tip is rotated at a desired speed during its passage through the stenosis. Once the obstruction is cleared, the coil is returned to its original smaller diameter and may be easily withdrawn from the vessel.

These and various other characteristics and advantages of the present invention will become readily apparent to those skilled in the art upon reading the following detailed description.

BRIEF DESCRIPTION OF THE DRAWINGS

For a detailed description of the preferred embodiments of the invention, reference will now be made to the accompanying drawings, wherein.

DETAILED DESCRIPTION OF THE PREFERRED EMBODIMENTS OF THE INVENTION

The drawings are illustrative of the apparatus of the present invention used for removing an obstruction from a vessel. The embodiments described are exemplary only, and can be modified in the practice of the invention.

Figure 1:
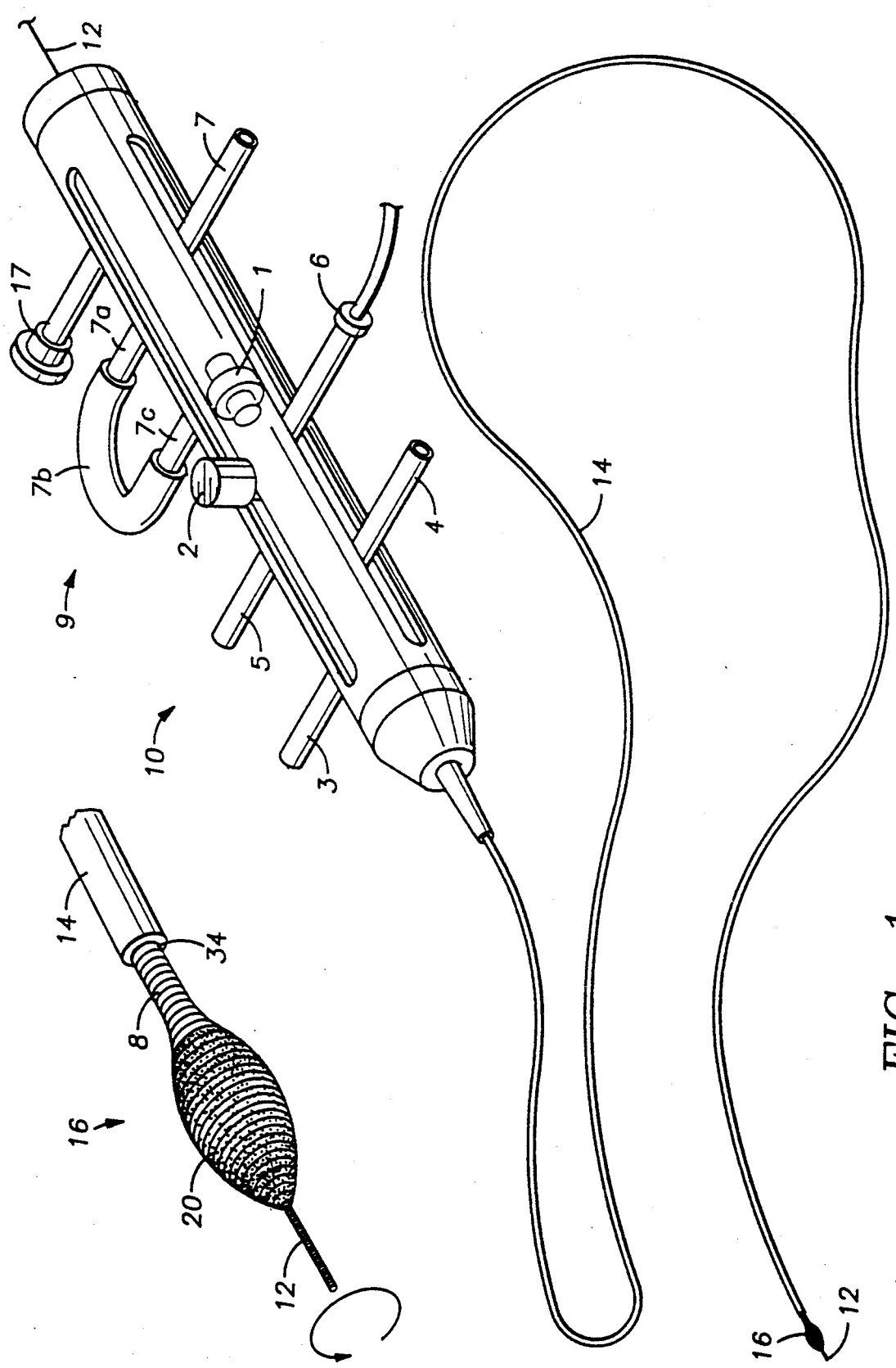
FIG. 1 is a schematic representation of the apparatus of the present invention with its drive-control unit at its proximal end and the drive coil, expandable tip, and guide wire disposed within the flexible outer catheter which surrounds the drive coil.

FIG. 1 is a schematic representation of one type of system 10 adapted for use with some of the preferred embodiments of the adjustable tip atherectomy device of the invention. A drive-control unit 9 is attached to one end of a flexible catheter 14 which surrounds a drive shaft coil 8. Drive shaft coil 8 is adapted for high speed rotation within the catheter 14. Flexible catheter 14 is made of a suitable biocompatible material capable of withstanding the heat of friction generated when drive shaft coil 8 is rotated at high speed. Speeds of rotation of drive shaft coil 8 within flexible catheter 14 of about 100,000 to 300,000 revolutions per minute are contemplated for the present invention, which speeds may be generated, for example, by means of a conventional compressed air turbine or the like. An expandable, adjustable diameter coil tip 16 is attached to drive shaft coil 8 at its distal end. The proximal end of the drive shaft coil 8 is attached to a torque drive device 1, such as the aforementioned compressed air turbine, which is centrally disposed within the drive-control unit 9. Actuation of the torque drive device 1 drives the drive shaft coil 8 which in turn rotates the expandable, adjustable diameter coil tip 16. The drive shaft coil 8 is preferably of a helically wound hollow wire configuration and is made of stainless steel or another suitable material capable of transmitting torque to drive the coil tip 16 at speeds as high as those referred to above which are contemplated for the present invention. Such helical coils with diameters as small as 0.032 inches have been used in the past for such high speed rotational torque transmission applications. Flexible catheter 14 assists in containing the forces acting on and transmitted by the drive shaft coil 8, and protects the body's intervening vasculature from injury or trauma during rotation of the drive shaft.

An air inlet port 7 of drive-control unit 9 accepts air from a conventional air pressure control unit (not shown) commonly found in hospital settings and well known to those skilled in the present art. Air at controlled pressure is applied momentarily and for the desired duration of tip rotation. The pressurized air passes through the inlet port 7 and communicates to the torque drive device inlet port 7c via air outlet port 7a and connecting tube 7b. Rotational speed is monitored by a conventional tachometer connected to tachometer cable connector 6 of drive-control unit 9. The air pressure control unit (not shown) may be adjusted to result in application of the desired air pressure to the turbine or the like to effect the desired tip rotational speed.

Drive-control unit 9 also includes several ports which communicate to various lumens of the overall atherectomy device of the present invention. Generally, the various lumens permit the injection through the device of fluids, such as medication, hydraulic actuation fluids for actuating the means for adjusting the expandable tip 16 of the device, and cooling fluids for reducing friction heating during high speed rotation, as further described below. Cooling fluids, for example, are introduced into the flexible catheter 14 around the drive shaft coil 8 to bathe the coil 8 during rotation.

In practice it is necessary to visualize the stenotic obstruction to be treated by the device of the present invention. This is accomplished by the injection of a contrast medium and fluoroscopic visualization as is commonly practiced by those skilled in the art. The atherectomy device of the present invention permits the injection of a contrast medium through central lumen 64 and the annular space 34, FIG. 1 and FIG. 2, created between the outer surface of the drive shaft coil 8 and the inner surface of flexible outer catheter 14. Port 3 of drive-control unit 9 communicates with the annular space 34 and, in addition to serving as a means for contrast medium injection, may be used to inject cooling fluid during high speed rotation. Port 4 of drive-control unit 9 communicates with central lumen 64, shown in FIG. 2, and may be used for the injection of a contrast medium, medication, and other fluids through the central lumen 64.

Figure 2:
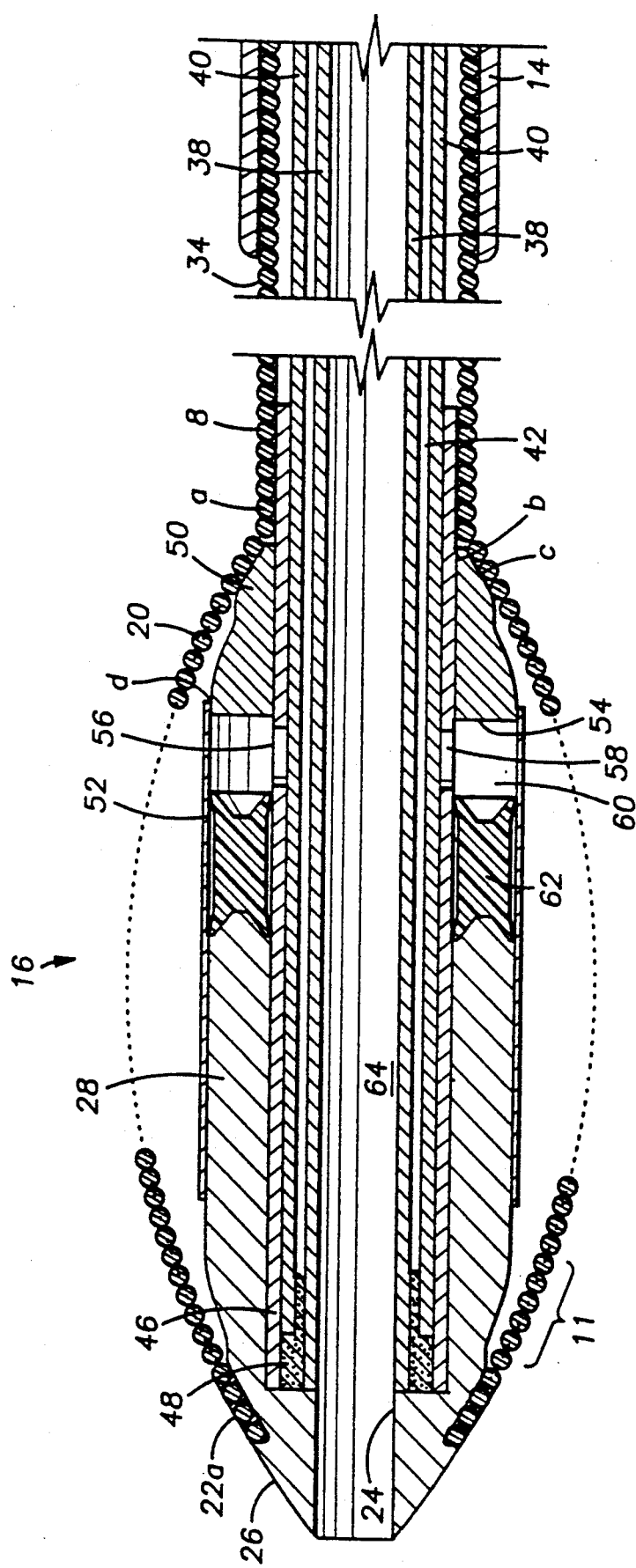
FIG. 2 is a length-wise cross sectional view of the expandable coil and the associated piston and inner catheter with the coil retracted and the coil circumference enlarged.

Referring to FIG. 2, it can be seen that central lumen 64 is created by a flexible catheter tube 38 which is disposed substantially concentrically and coaxially within a larger inner diameter flexible catheter tube 40. These concentrically and coaxially disposed inner catheters extend proximally within the passage created by the drive shaft coil 8 and extend beyond the proximal end of the drive shaft coil 8 within the drive-control unit 9. The concentric and coaxial disposition of flexible catheters 38 and 40 and the difference between the size of the outer diameter of catheter 38 and the inner diameter of catheter 40 creates an annular space lumen 42 which communicates to drive-control unit port 5, thus creating a passage for the purpose of activating the expanding means used to adjust the diameter of the ablating coil tip 16, as described further below.

The distal terminal ends of concentrically and coaxially disposed flexible catheters 38 and 40 are sealed by potting material 48 which serves to bond the tubes 38 and 40 together as well as to provide a distal seal for annular space lumen 42.

Central lumen 64 extends from the terminal distal end of tip 16 through drive-control unit 9 at its extreme proximal end. Thus the central lumen 64 can be used to guide the atherectomy device tip 16 of the present invention to a selected vessel obstruction by introduction over a prelocated guide wire 12, shown in FIG. 1.

The atherectomy device of the present invention is introduced into the body by way of the brachial or femoral artery, utilizing the Grunzig technique, which method is well known to those who practice in the area of catheterization. The device of the present invention minimizes damage to the vessel selected for catheter introduction. Normally, an introducer sheath is used to access the vessel at the point of introduction. Through the prepositioned introducer sheath is placed a guiding catheter and a guide wire appropriate for directing the atherectomy device of the present invention to the selected stenosis to be treated. The size, or diameter, of the introducer sheath and guiding catheter is determined by the size or diameter of the device to be introduced for treatment of the obstruction. Since existing atherectomy devices are of a fixed diameter, it is often necessary to introduce progressively larger diameter devices in order to fully clear a stenotic obstruction. This requires the use of introducer sheaths of a diameter sufficient to accept the larger diameter device, which results in greater vessel trauma at the point of vascular access. It is not uncommon, for example, to require use of introducer sheaths of up to a size 10F (10 French) in order to accommodate the desired diameter, for example about 2.25 to 2.5 millimeters, of prior art atherectomy tip. Applicant has even used a larger size introducer sheath, e.g., of size 11F (11 French), to accommodate a fixed diameter burr of about 2.75 to 3.0 millimeters, but to Applicant's knowledge, substantially no one else has used an introducer sheath so large as the 11F and a burr of the corresponding large size diameter without the need for balloon assistance for practicing the prior art atherectomy technique described above. In addition, as noted previously, the larger diameter atherectomy devices of the prior art may cause increased vascular tissue trauma as they are guided to the obstruction to be treated, and also may disturb, in passing, other, smaller vascular obstructions not otherwise indicated for treatment.

The present invention, due to its variable, adjustable diameter tip 16 may be introduced by the technique just described but can employ an introducer sheath and guiding catheter of a diameter that is less than its maximum expanded diameter. For example, it is contemplated that an introducer sheath of a size 6F, which is considerably smaller in diameter than the size 10F, can be used effectively with the expandable abrading tip of the present invention, even when removing obstructions that would require a 10F, 11F, or larger size sheath according to prior art techniques. This results in decreased vessel trauma at the vessel access site and also in decreased vessel trauma en route to the obstruction, which features offer a distinct advantage over existing atherectomy devices. The device of the present invention minimizes or avoids this vessel trauma because it is introduced and guided into position for treatment in its minimal diameter configuration.

Figure 3:
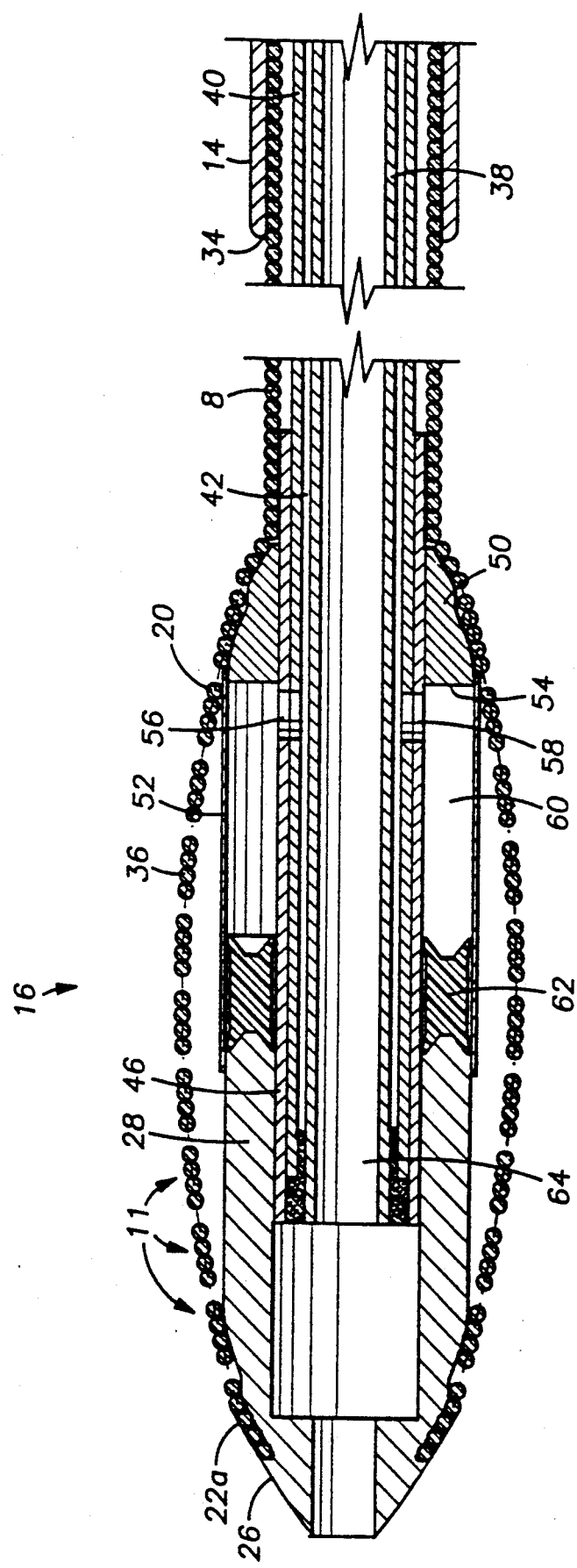
FIG. 3 is a length-wise cross sectional view of the coil of FIG. 2 in the elongated position with a smaller coil circumference.

Referring to FIGS. 2 and 3, the variable diameter feature of the abrading coil tip 16 of the invention will be described. FIG. 2 shows a piston means for one preferred embodiment of the dynamic variation of the abrading tip coil 20. FIG. 2 illustrates the abrading tip coil 20 in its maximum diameter condition and the activating means or piston in its deactivated condition. The piston is comprised of a proximal collar ring 50, a cylindrical piston inner sleeve 46, a cylindrical piston outer sleeve 52, a slidable piston seal ring 62, and a distal slidable piston collar 28 which also comprises the distalmost tapered abrading surface 26 of the device of the present invention.

The piston sleeves 46 and 52, the proximal collar 50, and the distal collar 28 are preferably made of stainless steel, but may be made of other materials suitable for the desired piston function and attachment described below.

Cylindrical piston inner sleeve 46 is attached to a number of the coil winds of drive shaft coil 8 at region "a" as well as to proximal collar 50 at region "b" by circumferential welding or the like. Outer piston sleeve 52 is circumferentially welded or the like to proximal collar 50 at region "d". Inner piston sleeve 46 is concentrically and coaxially disposed over flexible catheter tube 40 and bonded thereto to sealably fix the sleeve 46 around the flexible tube 40. The seal between inner piston sleeve 46 and flexible tube 40 is created by a tight slip fit between the members and by epoxy bonding or the like.

The distal piston collar 28 is slidably and rotationally free to move or telescope between inner piston sleeve 46 and outer piston sleeve 52. The slidable contacting surfaces of distal collar 28 and piston sleeves 46 and 52 may be deposited with a thin Teflon coating or the like to enhance the movement of distal collar 28 during piston function.

At the proximal termination of distal collar 28 and circumferentially disposed around inner piston sleeve 46 is slidable piston seal ring 62. Preferably made of Teflon or other suitable material, seal ring 62 is the primary piston "O" ring seal and is free to slide longitudinally axially between piston sleeves 46 and 52, thus creating a sliding seal between sleeves 46, 52.

Piston cavity 60 is an annular or circumferentially disposed, enclosed space bounded by the terminal distal face 54 of collar 50, the proximal terminal face of piston seal ring 62, the inner wall surface of sleeve 52, and the outer wall surface of sleeve 46.

Piston ports 56 and 58 access piston cavity 60. The ports 56, 58 are two, preferably, of a total of four piston ports that communicate through the wall of piston inner sleeve 46 and the wall of flexible tube catheter 40 to access annular space lumen 42.

Adjustable diameter, ovaloid shaped coils 20 of tip 16 are circumferentially disposed around the internal piston elements. The distal terminus of ovaloid coils 20 is attached to the piston distal collar at region 22a by circumferential welding or other suitable means. The distal attachment of coil 20 to distal collar 28 at region 22a is such that the attachment preferably forms a smooth continuation of the outer ovaloid surface of the tip 16. Thus, a smooth transition from the outer surface 26 of distal piston collar 28 to the coil 20 ovaloid surface is created.

Tightly wound ovaloid coil 20, by its attachment to distal piston collar 28 at region 22a and its attachment to proximal piston collar 50 at region "c", forms the piston's return spring.

As previously described, annular space lumen 42 communicates with port 5 of drive-control unit 9 and piston ports 56 and 58. Application of hydraulic pressure, or other suitable fluid pressure, at port 5 of drive-control unit 9 will transmit the necessary force to cause piston seal 62 to move distally and push slidable distal piston collar 28 in a forward or distal direction. As pressure at port 5 is increased, the major diameter of ovaloid coil 20 at the tip 16 decreases and the ovaloid outer shape lengthens or stretches to an increasingly right circular cylindrical configuration. As piston activation pressure increases, the ovaloid coil 20 stretches and unwinds under the pulling force exerted at region 22a by the distal movement of distal collar 28. The piston may be provided with a helical groove or the like, in which rides a radially outwardly projecting pin or the like disposed on the sleeve 46, to direct and channel the winding or unwinding movement of the coil winds as the piston is deactivated or activated, as the case may be.

FIG. 3 illustrates the effect of the piston activation at its maximum distal travel or movement. The ovaloid coil 20 shown in FIG. 3 comprises a quadrifilar coil which has been stretched and unwound in groups 36 of four winds per group when affected by the piston forces just described. Although a quadrifilar coil is shown, which coil stretches and unwinds also substantially as shown, other types or styles of coils, which stretch and unwind in other ways, may be used in the present invention.

The diameter of tip 16 can be varied from its maximum ovaloid diameter shown in FIG. 2 to its minimum elongated ovaloid diameter shown in FIG. 3. The dynamic diameter of the ovaloid tip 16 is a function of the piston activation pressure applied to piston cavity 60, and the return spring force of ovaloid coil 20. It is thus possible to select any desired tip diameter within the range bounded by the maximum and minimum diameters by selecting the appropriate piston activation pressure applied at port 5 of drive-control unit 9. The activation pressure can be set and monitored using standard gauges and pressure systems commonly used and well known to those of ordinary skill in the art.

Referring again to FIG. 1, there is shown on drive-control unit 9 a button 17 which serves as an air valve actuator to activate an air clamp which is centrally and proximally disposed within the drive-control unit 9. The air clamp is supplied by air from inlet port 7 and closes around and holds guide wire 12 in position at all times, except when the valve button is depressed. Thus the guide wire 12 is normally held during device rotation and released for advancement through the entire length of the atherectomy device.

The atherectomy device of the present invention will clear vascular stenoses by abrading or wearing away the stenotic material. The surface of the abrading tip 16 is deposited with particles, such as diamond dust 11, which may partially or totally cover the outer surface of ovaloid tip 16. The abrasive material surface may cover all or any portion, from the distalmost outer surface 26 of distal piston collar 28 to region "b" at the proximal termination of ovaloid tip 16.

The particle size of the abrading material should be substantially uniform over the abrading surface of the tip. Particle diameter size should be in the range of about 10 to about 100 microns, with a preferred sub-range of about 10 to about 20 microns. With abrading particles of about this size, rotated at the speeds contemplated for the present invention, the pieces of stenotic material abraded away will be about 5 to about 8 microns in diameter, which is less than the typical diameter of a red blood cell. At such a small particle size, the pieces of stenotic material abraded away can be disposed of naturally by the body through the capillary beds and there is no need for additional means of debris collection. Both soft and hard stenotic material may be removed by the cutting action of the tip 16.

Alternately, the abrading property of the surface of the tip 16 may be imparted by other methods, such as peening.

The tip 16 of the device of the present invention, unlike the tips of prior art devices, is preferably capable of abrading in both the forward and reverse progressions of the tip through a stenosis. This is due to the grit 11 preferably being deposited on both the leading and trailing slopes of the ovaloid tip 16.

Vascular recanalization of obstructions representing less than about 50% to 60% occlusion are not indicated. It has been found that the treatment for such occlusions by angioplasty or atherectomy more often aggravates the condition and accelerates the stenotic growth. In practice, those occlusions requiring treatment, the target stenoses, are not isolated, but rather are preceded by upstream and followed by downstream occlusions which preferentially should not be treated or should be bypassed by the treatment device.

Unlike existing atherectomy devices with fixed diameter ablators, the device of the present invention may be adjusted to its lower diameter and guided past and through non-target stenoses with reduced probability of aggravating these lesions.

Figure 4:
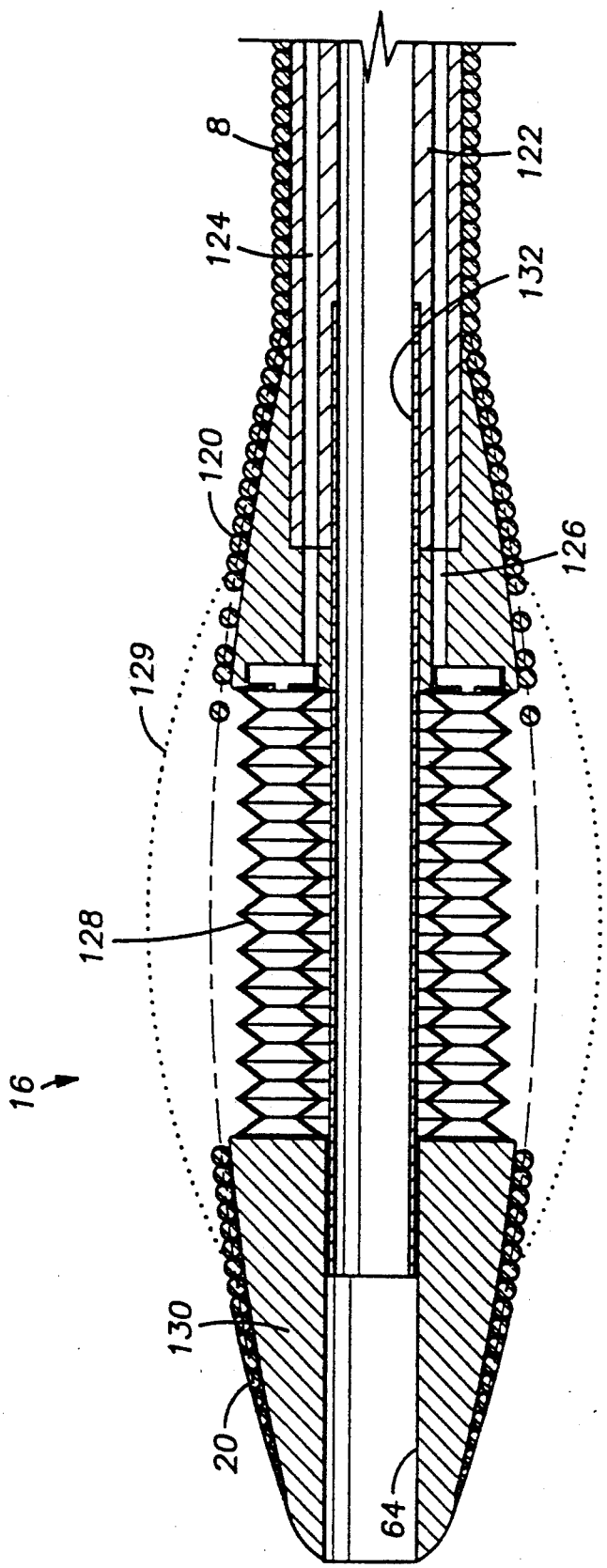
FIG. 4 is a length-wise cross sectional view of an alternative embodiment of the coil with a bellows associated with the coil for expansion.

Referring now to FIG. 4, there is shown a longitudinal cross sectional view of an alternative embodiment of the tip 16 of the atherectomy device of the present invention in which a bellows 128 is substituted for the piston as a means of ovaloid coil expansion. The bellows comprises a longitudinally expandable and contractible, hollow annular member having a plurality of accordion-like folds along its length. Bellows 128 is made of deposited nickel or other suitable thin walled material. Bellows 128 is attached at its proximal end to the distal face of a proximal collar 120, which in turn is attached to a plurality of winds of the coil 20 of tip 16 by circumferential welding or the like. A catheter tube 122 is sealably attached to the interior bore of the proximal end portion of collar 120. Catheter tube 122 preferably comprises a pair of concentrically and coaxially disposed flexible tubes forming an annular space lumen 124 therebetween. Catheter tube 122 is concentrically and coaxially disposed within drive shaft coil 8. Annular space lumen 124 communicates through passages 126 in collar 120 to the interior of bellows 128 at its proximal end. The distal end of bellows 128 is attached to the proximal face of a slidable distal tip collar 130. A plurality of winds of the coil 20 at its distal end are attached to the outer surface of the tip 130 by circumferential welding or the like. A metal guide tube 132 is attached within and to the distal end of the catheter tube 122, and projects therefrom through the bellows and into the central axial bore of the tip 130. The tip 130 is free to slide rotationally and longitudinally axially on the guide tube 132. Upon application of activation pressure, longitudinal expansion of the bellows 128 causes the tip coil 20 to stretch, reducing its circumference or diameter in a manner similar to that described in connection with the embodiment shown in FIGS. 2 and 3. Removal of the activation pressure will cause the bellows to contract, because of the spring effect associated with the metal bellows configuration. When the bellows is in its contracted state, the diameter of the ovaloid tip 16 is at its maximum, and when the bellows is in its expanded state, the diameter of the tip is at its minimum. FIG. 4 illustrates the bellows in its expanded state. The increased diameter of the coil when the bellows is in its contracted state is indicated in the central portion of the figure by the dotted lines 129.

Figure 5:
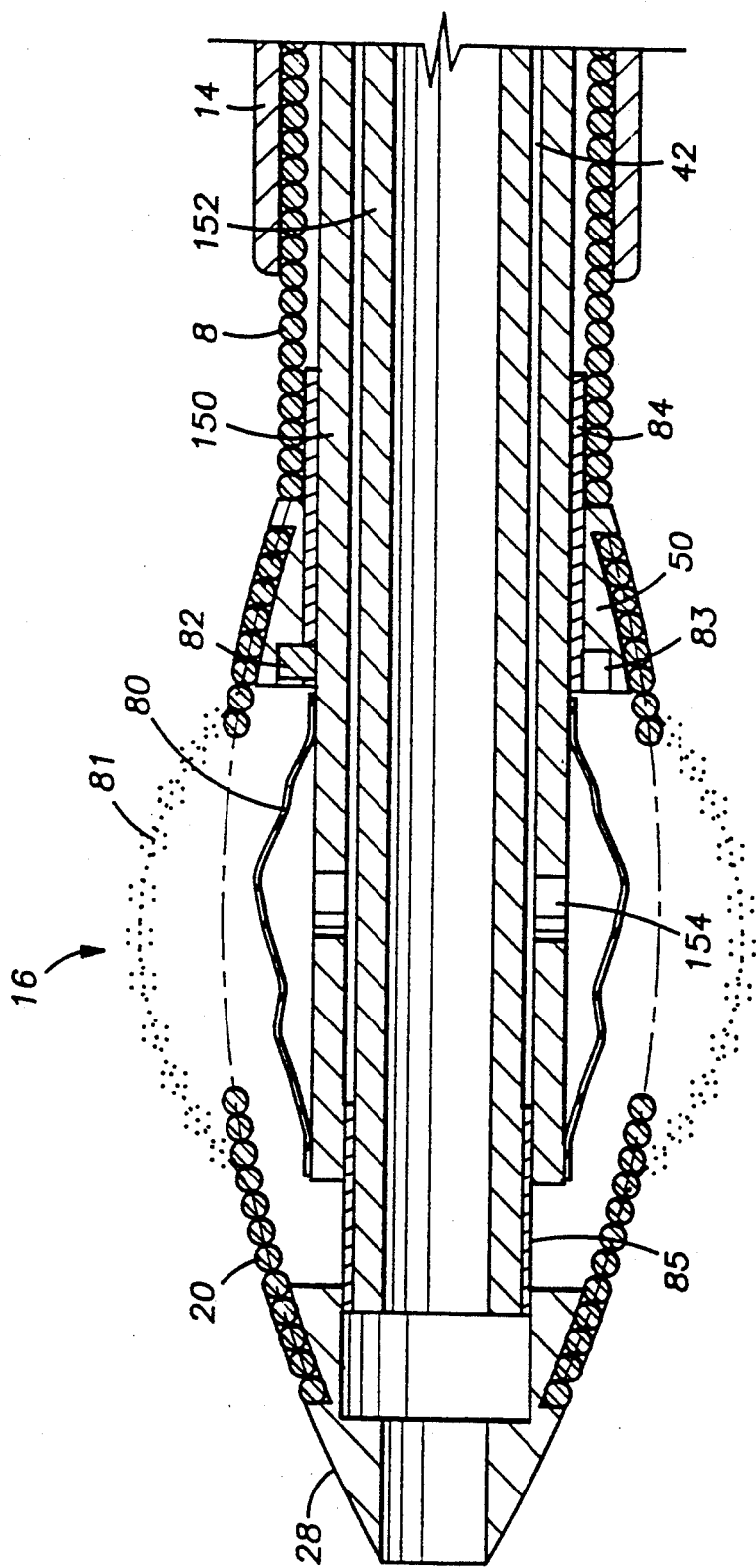
FIG. 5 is a length-wise cross sectional view of an alternative embodiment with an inflatable balloon used for coil expansion.

Referring to FIG. 5, there is shown a cross sectional view of an alternative embodiment of the tip 16 in which a high pressure balloon 80, such as those commonly used in angioplasty devices, is used as the tip coil expansion means. In this embodiment the tip 16 is normally in its minimum diameter condition. As in the previously described embodiments, the annular space lumen 42 conveys the pressure required to expand the balloon 80. As the balloon 80 expands, it expands the associated central portion of the tip coil 20. This results in a tip diameter increase that simultaneously changes the ovaloid shape of the tip 16 to a modified ovaloid shape having a compound ovaloid or distended central portion 81.

As seen in FIG. 5, this embodiment may incorporate a pin 82 which rides in a 350° slot 83 which is circumferentially disposed around the inner wall surface of a proximal collar 50. The pin is fixed to a proximal metal slide tube 84 by welding or the like. The proximal metal slide tube 84 is disposed around an outer catheter tube 150. The proximal collar 50 is rotationally free to move over the surface of proximal metal slide tube 84 and may rotate a total of 350°, at which time it engages the drive pin 82. The drive shaft coil 8 is weldably or otherwise attached to the proximal metal slide tube 84 and thus may drive the proximal collar 50 during high speed rotation. A distal collar 28 is weldably or otherwise attached to a plurality of winds of coil 20 at its distal end, and the proximal collar 50 is weldably or otherwise attached to a plurality of winds of coil 20 at its proximal end. A metal slide tube 85 is mounted around the distal end of an inner catheter tube 152, and is telescoped into a central axial counterbore in the proximal face of the distal collar 28. The metal slide tube 85 is sealably disposed between the catheter tubes 150, 152 and seals the distal ends of the tubes 150, 152 The lumen 42 between the catheter tubes 150, 152 communicates through ports 154 in the outer catheter tube 150 to the interior of balloon 80, which is mounted on the outer surface of the outer catheter tube 150. Air is introduced through the ports 154 to inflate the balloon 80. The distal collar tip 28 is free to slide longitudinally axially and rotationally over the surface of metal slide tube 85, and collar 50 is free to rotate over the surface of its associated slide tube 84. Thus the coil 20 of tip 16 may unwind and wind as the coil expands and contracts, as the case may be, under the action of the balloon 80. The balloon 80 at its maximum inflation forces the center of the ovaloid to its maximum diameter. Removing the air pressure from the balloon causes it to deflate, allowing the coil to return to its normal, reduced diameter state.

Figure 6:
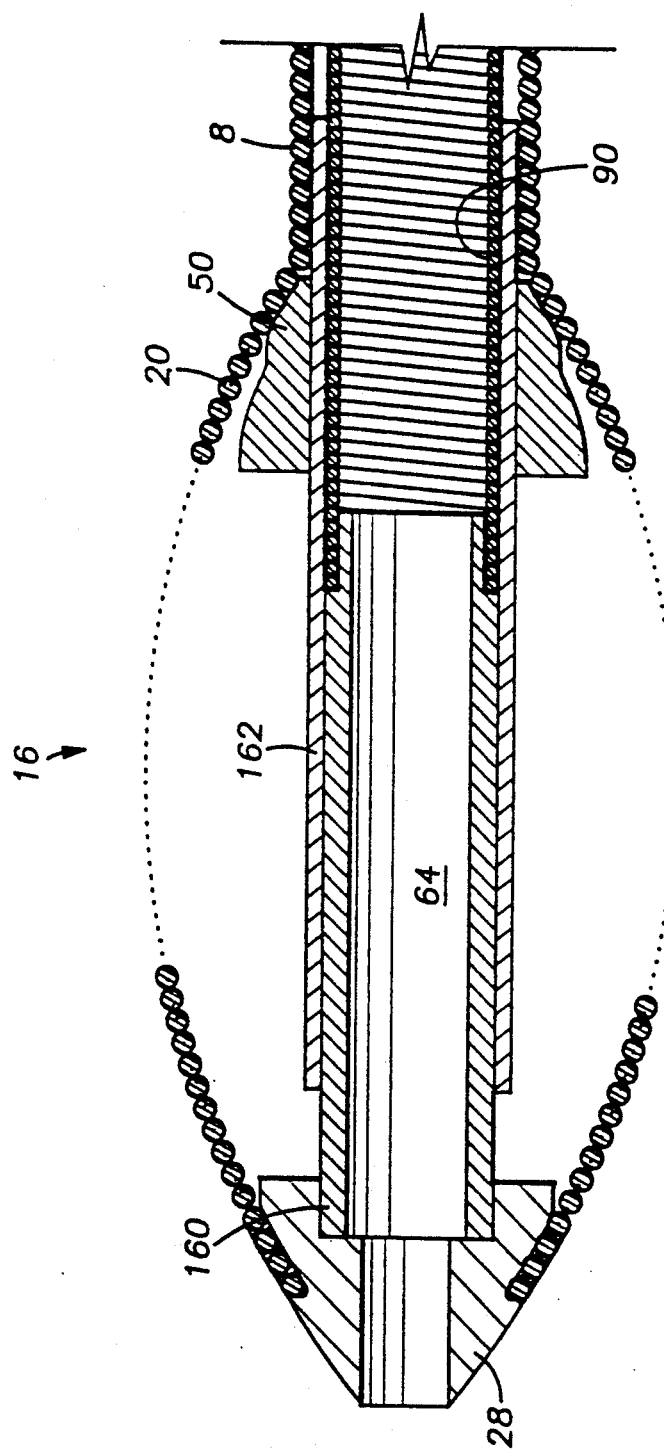
FIG. 6 is a length-wise cross sectional view of an alternative embodiment with a pair of concentrically and coaxially disposed, telescopingly slidable sleeves disposed within the coil and cooperable to effect coil expansion.

FIG. 6 is a cross sectional view of an alternative embodiment in which a second helical coil 90 is coaxially and centrally disposed within the drive shaft coil 8. The innermost coil 90 is free to slide within the drive shaft coil 8 and extends through the entire length of the device. A pair of such coils as manufactured by Lake Region Manufacturing Company, Inc. of Chaska, Minn., may be found suitable for use in this embodiment, but other or equivalent coils can of course be used. The distal end of the inner coil 90 is attached to the distal tip collar 28 through an inner slide sleeve 160. The ovaloid tip 16 coil 20 is attached to the distal and proximal collars 28, 50 as previously described. An outer slide sleeve 162 is telescoped over the inner slide sleeve 160 and is disposed at its proximal end within the central axial bore of the proximal collar 50. The inner slide sleeve 160 is free to telescope longitudinally axially within, and to rotate within, the outer slide sleeve 162.

The tip 16 of FIG. 6 is normally in its maximum diameter condition and is caused to reduce its diameter by the longitudinal movement of the inner coil 90 within the drive shaft coil 8 in a distal direction. When the inner coil 90 is pushed and/or rotated distally within the drive shaft coil 8 the distal tip collar 28 moves forward, in relation to proximal collar 50 and causes the tip coil 20 to stretch. Thus the tip diameter may be reduced. The tip 16 diameter in this embodiment is a function of the longitudinal displacement of the distal collar 28 with respect to the proximal collar 50. The tip coil 20 for this embodiment may be a continuation of the drive shaft coil 8, as shown in FIG. 2, or an individual coil segment, as shown in FIG. 5.

Figure 7:
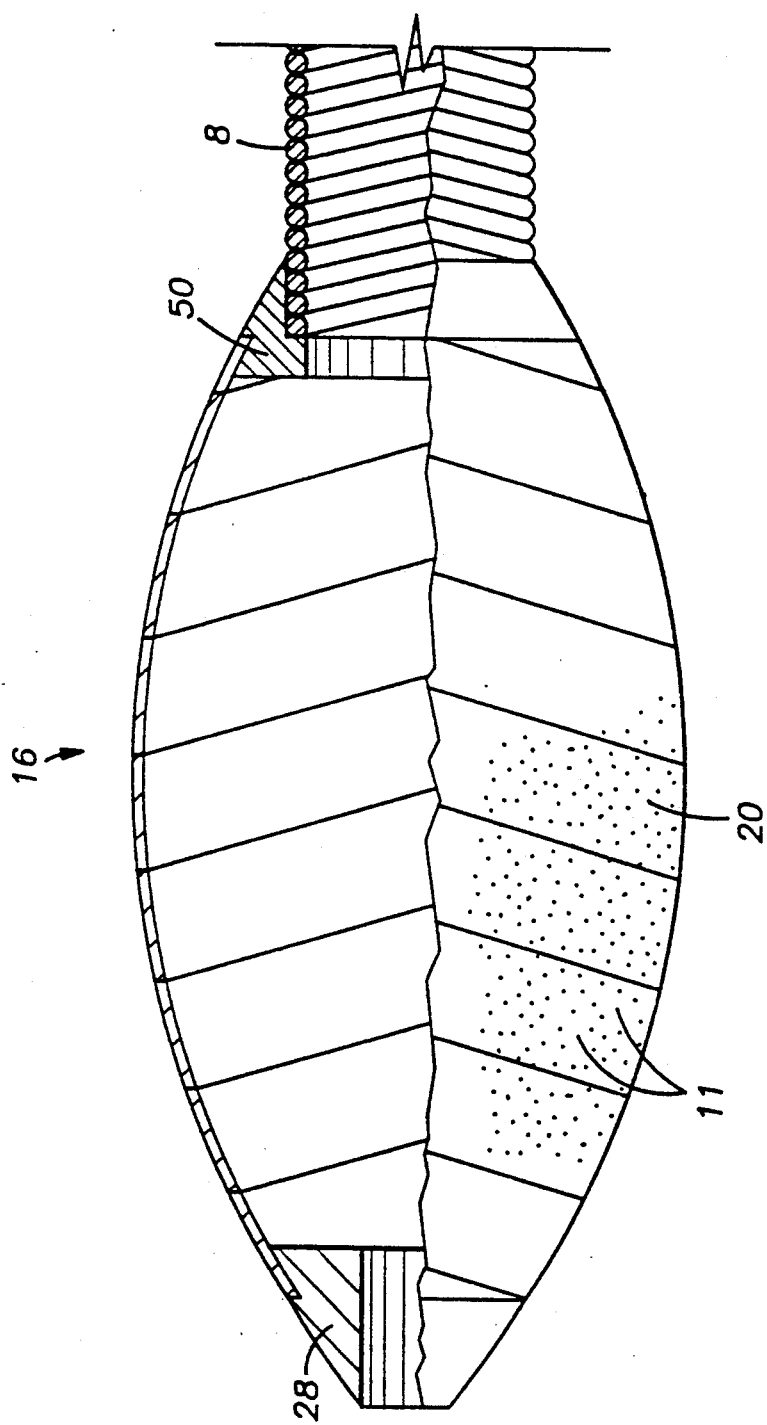
FIG. 7 is a length-wise cross sectional view of an alternative embodiment of the expandable coil wherein the coil comprises a helically wound ribbon-like metal strip.

Alternatively, the coil 20 of ovaloid tip 16 may be replaced by a deposited metal ovaloid such as nickel, preferably having a wall thickness of less than 0.002 inches. Further, the coil feature of the deposited metal tip may be cut into the previously deposited ovaloid shape such that the coil ribbons at the center, or apex, of the ovaloid are widest and decrease in width as the ovaloid slope descends to the distal and proximal minor ovaloid diameters. There may be one helix, or a plurality of adjacent helices, comprising the coil. The deposited metal coil alternative presents what may be described as a "lemon peel" feature. An illustration of such an embodiment is shown, for example, in FIG. 7.

While preferred embodiments of the invention have been described, various modifications can be made to the preferred embodiments without departing from the principles of the present invention.

We claim:

1. An apparatus for removing an obstruction from a vessel, comprising:
   a coil;
   said coil being capable of elongation thereby reducing the circumference as said coil is elongated;
   means for selectively elongating said coil;
   means for introducing said coil inside a vessel proximate to an obstruction;
   said coil having an abrasive surface covering at least part of its outer surface; and
   means for selectively rotating said coil.

2. An apparatus for removing an obstruction from a vessel according to claim 1, wherein said coil is of substantially ovaloid configuration prior to elongation.

3. An apparatus for removing an obstruction from a vessel according to claim 1, wherein approximately all of the outer surface of said coil is an abrasive surface.

4. An apparatus for removing an obstruction from a vessel, comprising:
   a coil;
   the circumference of said coil being capable of enlargement by unwinding and compressing the coil;

means for selectively unwinding and compressing said coil for effecting such enlargement of the circumference of said coil;

means for introducing said coil in the vessel proximate to the obstruction;

said coil having an abrasive surface covering at least part of its outer surface; and means for selectively rotating said coil.

5. An apparatus for removing an obstruction from a vessel according to claim 4, wherein approximately all of the outer surface of said coil is an abrasive surface.

6. An apparatus for removing an obstruction from a vessel, comprising:

a length of coil preformed in an ovaloid shape;

means for rotating said length of coil;

said length of coil having an abrasive surface covering at least a part of its outer surface;

a tubular catheter with a central lumen;

said catheter terminating in a tip with an opening in said tip communicating with the central lumen of said catheter;

said length of coil surrounding the terminal end of said catheter with the terminal end of said length of coil fixed to the terminal end of said tip of said catheter;

means for elongating said length of coil thereby reducing the circumference of said length of coil; and said elongation means being disposed between said catheter and said length of coil.

7. An apparatus for removing an obstruction from a vessel according to claim 6, wherein said means for rotating said length of coil comprises a drive shaft coil powered to rotate said ovaloid length of coil at selected speeds from 0 rpm up to about 300,000 rpm.

8. An apparatus for removing an obstruction from a vessel according to claim 6, wherein said length of coil is comprised of multifilar coil wire.

9. An apparatus for removing an obstruction from a vessel according to claim 6, wherein said length of coil is comprised of a wire with a flat outer surface.

10. An apparatus for removing an obstruction from a vessel according to claim 6, wherein said length of coil is comprised of a wire with a rounded outer surface.

11. An apparatus for removing an obstruction from a vessel according to claim 6, wherein said length of coil is comprised of a coil of deposited metal having ribbon-shaped winds.

12. An apparatus for removing an obstruction from a vessel according to claim 6, wherein said abrasive surface covers the approximate half of said length of coil adjacent to said tip of said catheter.

13. An apparatus for removing an obstruction from a vessel according to claim 6, wherein said abrasive surface covers the approximate half of said length of coil adjacent to said tip of said catheter and the entire exposed surface of said tip of said catheter.

14. An apparatus for removing an obstruction from a vessel according to claim 6, wherein said abrasive surface covers approximately all of the outer surface of said length of coil.

15. An apparatus for removing an obstruction from a vessel according to claim 6, wherein said abrasive surface covers approximately all of the outer surface of said length of coil and the exposed outer surface of said tip of said catheter.

16. An apparatus for removing an obstruction from a vessel according to claim 6, wherein said abrasive surface is selected from the group of diamond particles, synthetic diamond particles or a peened surface.

17. An apparatus for removing an obstruction from a vessel according to claim 6, wherein said tubular catheter is comprised of a flexible biocompatible material.

18. An apparatus for removing an obstruction from a vessel according to claim 17, wherein said coil is comprised of a wire with a rounded outer surface.

19. An apparatus for removing an obstruction from a vessel according to claim 17, wherein said coil is comprised of a coil of deposited metal having ribbon-shaped winds.

20. An apparatus for removing an obstruction from a vessel according to claim 17, wherein said abrasive surface covers the approximate half of said coil adjacent to said tip of said catheter.

21. An apparatus for removing an obstruction from a vessel according to claim 17, wherein said abrasive surface covers the approximate half of said coil adjacent to said tip of said catheter and the entire exposed surface of said tip of said catheter.

22. An apparatus for removing an obstruction from a vessel according to claim 17, wherein said abrasive surface covers approximately all of the outer surface of said coil.

23. An apparatus for removing an obstruction from a vessel according to claim 17, wherein said abrasive surface covers approximately all of the outer surface of said coil and the exposed outer surface of said tip of said catheter.

24. An apparatus for removing an obstruction from a vessel according to claim 17, wherein said abrasive surface is selected from the group of diamond particles, synthetic diamond particles or a peened surface.

25. An apparatus for removing an obstruction from a vessel according to claim 17, wherein said expandable means is comprised of a balloon that can be selectively inflated and deflated.

26. An apparatus for removing an obstruction from a vessel of claim 17, wherein at least one end of said coil is fixed to said catheter.

27. An apparatus for removing an obstruction from a vessel according to claim 6, wherein said elongation means is comprised of a remotely actuated piston engageable with said length of coil to retract and extend said length of coil to and from the ovaloid shape.

28. An apparatus for removing an obstruction from a vessel according to claim 6, wherein said elongation means is comprised of a remotely actuated bellows engageable with said length of coil to retract and extend said length of coil to and from the ovaloid shape.

29. An apparatus for removing an obstruction from a vessel according to claim 6, wherein said tubular catheter comprises an inner flexible catheter coil substantially concentrically and coaxially disposed within an outer flexible drive shaft coil, said tip of said tubular catheter being fixed to the terminal end of said inner flexible catheter coil, said terminal end of said length of coil which is attached to said tip of said tubular catheter being the distal end of said length of coil, said means for rotating said length of coil comprising said outer flexible drive shaft coil, said outer flexible drive shaft coil being fixed to the proximal end of said length of coil, said elongation means comprising an inner slide sleeve fixed at its distal end to said tip of said catheter and at its proximal end to said inner flexible catheter coil, an outer slide sleeve rotationally and longitudinally axially slidably disposed around said inner slide sleeve, the proximal end of said outer slide sleeve being disposed within said proximal end of said length of coil, said inner flexible catheter coil being longitudinally axially movable within said outer drive shaft coil.

30. An apparatus for removing an obstruction from a vessel according to claim 6, wherein said tubular catheter is comprised of a flexible biocompatible material.

31. An apparatus for removing an obstruction from a vessel, comprising:
- a coil capable of an enlarged circumference forming a bulge in said coil after partial unwinding and compression of said coil;
- said coil having an abrasive surface covering at least part of its outer surface;
- means for rotating said coil;
- a tubular catheter with a central lumen;
- said catheter terminating in a tip with an opening in the tip communicating with the central lumen of the catheter;
- said coil surrounding the terminal end of said catheter;
- an expandable means disposed between said catheter and said coil and engageable with the inner surface of said coil when activated to expand said coil and allow the free end of said coil to unwind and at the same time to allow for compression of the length of said coil thereby enlarging the circumference and diameter of said coil, and upon deactivation contracting away from said inner surface of said coil allowing said coil to rewind and assume its smaller circumference and diameter; and
- means for remotely activating the expandable means to selectively increase and decrease the diameter of said coil.

32. An apparatus for removing an obstruction from a vessel according to claim 31, wherein said means for rotating said coil comprises a drive shaft coil powered to rotate said expandable coil at selected speeds from 0 rpm up to about 300,000 rpm.

33. An apparatus for removing an obstruction from a vessel according to claim 31, wherein said coil is comprised of miltifilar coil wire.

34. An apparatus for removing an obstruction from a vessel according to claim 31, wherein said coil is comprised of a wire with a flat outer surface.

35. An apparatus for removing an obstruction from a vessel, comprising:
- a coil;
- the diameter of said coil being changeable by winding and unwinding said coil;
- means for selectively winding and unwinding said coil for effecting such change in diameter of said coil;
- means for introducing said coil in the vessel proximate to the obstruction;
- said coil having an abrasive surface covering at least part of its outer surface; and
- means for selectively rotating said coil.

36. A method for removing an obstruction from a vessel, comprising the steps of:
- introducing a variable diameter coil with an abrasive surface covering at least part of its outer surface into the vessel proximate to the obstruction in a reduced coil diameter state;
- unwinding the coil at the site of the obstruction to increase the diameter of the coil;
- rotating the increased diameter coil at high speed to abrade away the obstruction;
- subsequent to such high speed rotation, rewinding the coil to reduce its diameter; and
- withdrawing the coil from the vessel.

37. A method for removing an obstruction from a vessel according to claim 36, comprising the additional step, prior to the introducing step, of winding the coil to reduce its diameter.

38. A method for removing an obstruction from a vessel, comprising the steps of:
- introducing a variable diameter coil with an abrasive surface covering at least part of its outer surface into the vessel proximate to the obstruction in a reduced coil diameter state;
- axially compressing the coil at the site of the obstruction to increase the diameter of the coil;
- rotating the increased diameter coil at high speed to abrade away the obstruction;
- subsequent to such high speed rotation, axially elongating the coil to reduce its diameter; and
- withdrawing the coil from the vessel.

39. A method for removing an obstruction from a vessel according to claim 38, comprising the additional step, prior to the introducing step, of axially elongating the coil to reduce its diameter.

40. A method for removing an obstruction from a vessel, comprising the steps of:
- introducing a variable diameter coil with an abrasive surface covering at least part of its outer surface into the vessel proximate to the obstruction in a reduced coil diameter state;
- activating an expansion means disposed within said coil into expanding engagement with the interior of said coil to increase its diameter;
- rotating the increased diameter coil at high speed to abrade away the obstruction;
- subsequent to such high speed rotation, deactivating the expansion means to remove it from expanding engagement with the interior of said coil to reduce its diameter; and
- withdrawing the coil from the vessel.

* * * * *